United States Patent [19]

Weinrotter et al.

[11] 4,008,234

[45] Feb. 15, 1977

[54] PROCESS FOR THE PREPARATION OF MELON

[75] Inventors: Ferdinand Weinrotter; Karlheinz Wegleitner, both of Linz; Walter Müller, Leonding, all of Austria

[73] Assignee: Chemie Linz Aktiengesellschaft, Linz, Austria

[22] Filed: Aug. 1, 1975

[21] Appl. No.: 601,135

[30] Foreign Application Priority Data

Aug. 7, 1974 Austria .............................. 6469/74

[52] U.S. Cl. ........................................... 260/249.6
[51] Int. Cl.² ..................................... C07D 251/72
[58] Field of Search ................................. 260/249.6

[56] References Cited

OTHER PUBLICATIONS s-Triazines and Derivatives, Smolin et al., Interscience Pub. Inc., New York (1959 pp. 468–469.

*Primary Examiner*—John M. Ford
*Attorney, Agent, or Firm*—Wenderoth, Lind & Ponack

[57] ABSTRACT

Melon is prepared by heating, in the solid form, preferably as granules, a mixture of dicyandiamide and melamine, or a mixture of one or both thereof with urea and/or biuret and/or triuret and/or guanidine carbonate at a temperature from 450° to 600° C.

16 Claims, No Drawings

PROCESS FOR THE PREPARATION OF MELON

This invention relates to a process for the preparation of melon.

If dicyandiamide or melamine in powdered form is heated to a temperature of 500° to 600° C until the evolution of ammonia ceases, melon, a compound having the following formula:-

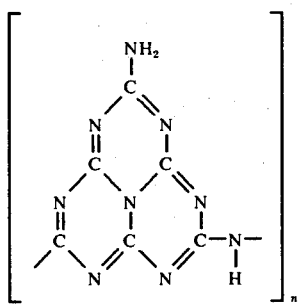

wherein $n$ is an integer greater than 1, is obtained in a moderate yield, which is used to an increasing extent instead of poisonous cyanides in quenching baths. The production of melon on an industrial scale has hitherto provide impracticable, not only because when the powdered starting products are melted in suitable apparatus large amounts of difficultly removable incrustations are formed from a wide variety of pyrolysis products, but also because a proportion of the said starting products sublimes without reacting. In addition, during the heating irregularly shaped aggregates of different sizes are formed which are more or less porous as a result of the escape of ammonia and in which further reaction to form melon no longer takes place on account of the poor conduction of heat within acceptable reaction times.

Surprisingly, it has now been found that melon may be prepared on an industrial scale with unexpectedly high yields and a high level of purity, in a simple way in a single process step, by starting not with melamine or dicyandiamide alone but from a solid mixture, for example, in the form of granules, of both substances, which may be considered as oligomers of cyanamide, or from one of the two substances or a mixture of both substances with urea and/or a condensation product thereof, i.e. biuret and/or triuret, and heating them at a temperature of 450° to 600° C. Satisfactory results also are obtained if guanidine carbonate, optionally with urea and/or biuret and/or triuret, is heated with melamine or dicyandiamide or a mixture thereof, for example, in the form of granules. Accordingly the present invention provides a process for the preparation of melon, which comprises heating, in the solid form, formed mixtures of dicyandiamide and melamine, or a mixture of one or both thereof with urea and/or a biuret and/or triuret and/or guanidine carbonate at a temperature from 450° to 600° C.

A particular advantage of the process of the present invention is that the melon obtained has the same uniform compact form in which the original reaction mixture, preferably formed into granules, existed, and accordingly the amount of dust may be kept substantially lower, even on an industrial scale, than is the case in the hitherto conventional production on a laboratory scale. Depending on the composition of the mixtures and the reaction temperature, the yields of melon are from 65 to 90% based upon the starting melamine and/or dicyandiamide. Since the by-products formed in addition to melon sublime under the conditions of the process according to the invention, the purity of the end product obtained is always excellent.

In performing the process of the invention the starting mixture is preferably used in the form of granules, optionally after additional grinding.

The optimum heating temperature is within the range of from 500° to 570° C and the preferred heating time is from 15 minutes to 6 hours, more preferably from 30 minutes to 2 hours.

If the starting materials used in the process according to the invention are melamine and dicyandiamide, the preferred mixture ratio is from 10 : 1 to 1 : 10, more preferably from 6 : 1 to 1 : 1.

If the starting materials are melamine and/or dicyandiamide on the one hand, and urea and/or biuret and/or triuret and/or guanidine carbonate on the other hand, the mixture ratio between the two groups of substances is preferably from 1 : 1 to 20 : 1, more preferably from 3 : 1 to 10 : 1.

The advantage of also using mixtures of several of the said substances for the preparation of melon in the manner described above is evident. If a solid mixture of urea and guanidine carbonate is formed, for example, in the processing of mother liquors which contain urea and guanidine among other things, this may be used directly without any further processing for the production of melon. Likewise, a mixture of biuret or triuret with melamine, for example, also gives good melon yields if it still contains large amounts of urea (starting product).

The preferred grain size of the granules or prills which are advantageously used, is 1 mm to 2 cm, more preferably 3 mm to 1 cm.

It has been found to particularly suitable to use mixtures of melamine and/or dicyandiamide with urea, wherein powdered melamine or dicyandiamide also may be granulated in a conventional manner with urea solutions.

The preferred concentration of the aqueous urea solution employed is in this case from 20 to 80% by weight, more preferably from 50 to 70%.

The following Examples illustrate the invention and the manner in which it may be performed.

EXAMPLE 1

150 kg of powdered melamine and dicyandiamide were formed in a conventional manner in a ratio of 3 : 1 into granules having a diameter of 0.5 cm, and the granules were heated in a drying drum for 1 hour at a temperature of 560° C. Melon was obtained having approximately the same granule size as the starting material, and in an approximately 70% yield based upon the melamine-dicyandiamide mixture initially employed.

EXAMPLE 2

50 kg of melamine were granulated with biuret in a ratio of 3 : 1 and heated for 45 minutes at a temperature of 500° C. The yield of melon was 81.5% referred to melamine. If half the biuret is replaced by triuret, there is no change in the yield and purity of the end product. Similarly, the melamine may be wholly or partially replaced by dicyandiamide without any loss in yield.

EXAMPLE 3

200 kg of powdered dicyandiamide were granulated in a conventional manner with urea in a ratio of 5 : 1 and heated at a temperature of 530° C for 75 minutes. The melon yield is 75% based upon the dicyandiamide used. If a corresponding amount of cyanamide and urea is used, the yield and purity of the end product are the same because cyanamide dimerises to dicyandiamide and consequently dicyandiamide may be considered to be the actual starting product.

EXAMPLE 4

A mixture of biuret and triuret is obtained in a conventional manner from urea by heating. This mixture is granulated with 100 kg of dicyandiamide in a ratio of 1 : 3 and is heated for one hour at 400° C and for a further hour at 560° C.

The yield and purity of melon based upon dicyandiamide were comparable to those obtained in the above Examples. The same is true if the biuret-triuret mixture is replaced by guanidine carbonate and this is heated in the specified mixture ratio and under the same reaction conditions with dicyandiamide and/or melamine.

EXAMPLE 5

500 kg of melamine were granulated with a 65% urea solution. The granules formed contained 10% urea. These granules were dried and then heated in a muffle furnace at 560° C for one hour. The melon yield was 78% based upon tje melamine used. With the urea content of 17% and heating at 560° C for one hour, the melon yield was 84% based upon the melamine used, and the purity was high. Conventional apparatus such as granulation plates or drums may be used for the granulation. For the reaction itself many different types of furnace may likewise by used, such as, for example, a muffle furnace, shelved furnace, rotatory furnace or tunnel furnace.

What we claim is:

1. A process for the preparation of melon which comprises heating solid, formed mixtures of at least two compounds selected from the group consisting of dicyandiamide, melamine, urea, biuret, triuret and guanidine carbonate at a temperature from 450° to 600° C, whereby these mixtures must contain at least one compound selected from the group consisting of dicyandiamide and melamine.

2. A process according to claim 1, in which the starting mixture is in the form of granules.

3. A process according to claim 1, in which the heating temperature is within the range of 500° to 570° C.

4. A process according to claim 1, in which the heating time is 15 minutes to 6 hours.

5. A process according to claim 4, in which the heating time is half-an-hour to 2 hours.

6. A process according to claim 1, in which the mixture ratio between melamine and dicyandiamide is 10 : 1 to 1 : 10.

7. A process according to claim 6, in which the said ratio is 6 : 1 to 1 : 1.

8. A process according to claim 1 in which the starting mixture is (1) a member selected from the group consisting of dicyandiamide, melamine and mixtures thereof in combination with (2) a member selected from the group consisting of urea, biuret, triuret, guanidine carbonate and mixtures thereof wherein the compounds of (1) and (2) are in a mixture ratio of 1 : 1 and 20 : 1.

9. A process according to claim 8 in which the starting mixture is in the form of granules having a grain size of 1 mm to 2 cm and in which the heating time is 15 minutes to 6 hours.

10. A process according to claim 8, in which the said ratio is 3 : 1 to 10 : 1.

11. A process according to claim 2, in which the grain size of the granules is from 1 mm to 2 cm.

12. A process according to claim 11, in which the grain size is from 3 mm to 1 cm.

13. A process according to claim 2, in which the starting mixture comprises a member selected from the group consisting of melamine, dicyandiamide and mixtures thereof with urea.

14. A process according to claim 13, in which the starting mixture is in the form of granules produced by granulating powdered melamine or dicyandiamide with an aqueous solution of urea.

15. A process according to claim 14 in which the concentration of the aqueous solution of urea solutions is 20 to 80% by weight.

16. A process according to claim 15 in which the said concentration is 50 to 70% by weight.

* * * * *